(12) United States Patent
Ates et al.

(10) Patent No.: US 8,957,226 B2
(45) Date of Patent: Feb. 17, 2015

(54) 2-OXO-1-PYRROLIDINE DERIVATIVES, PROCESSES FOR PREPARING THEM AND THEIR USES

(75) Inventors: Celal Ates, Louvain-la-Neuve (BE); Francoise Lurquin, Villers-la-Ville (BE); Yannick Quesnel, Wavre (BE); Arnaud Schule, Braine-l'Alleud (BE)

(73) Assignee: UCB Pharma S.A., Brussels (BE)

( * ) Notice: Subject to any disclaimer, the term of this patent is extended or adjusted under 35 U.S.C. 154(b) by 1507 days.

(21) Appl. No.: 11/992,065

(22) PCT Filed: Sep. 12, 2006

(86) PCT No.: PCT/EP2006/008852
§ 371 (c)(1),
(2), (4) Date: Jul. 15, 2009

(87) PCT Pub. No.: WO2007/031263
PCT Pub. Date: Mar. 22, 2007

(65) Prior Publication Data
US 2009/0318708 A1    Dec. 24, 2009

(30) Foreign Application Priority Data

Sep. 15, 2005 (EP) .................................... 05020080
Oct. 24, 2005 (EP) .................................... 05023133

(51) Int. Cl.
*C07D 207/267* (2006.01)
*C07D 207/27* (2006.01)

(52) U.S. Cl.
CPC .......... *C07D 207/267* (2013.01); *C07D 207/27* (2013.01)
USPC ......................................... 548/550; 548/543

(58) Field of Classification Search
CPC ......................... C07D 207/267; C07D 207/27
USPC .................................................. 548/550, 543
See application file for complete search history.

(56) References Cited

U.S. PATENT DOCUMENTS

| | | | | |
|---|---|---|---|---|
| 7,244,747 B2 * | 7/2007 | Kenda et al. | .................. | 514/338 |
| 7,381,747 B2 * | 6/2008 | Dooley et al. | ................. | 514/567 |
| 7,763,644 B2 * | 7/2010 | Kenda et al. | .................. | 514/394 |
| 2003/0040631 A1 * | 2/2003 | Surtees et al. | ................ | 548/517 |
| 2004/0204476 A1 * | 10/2004 | Ates et al. | ..................... | 514/424 |
| 2005/0137241 A1 * | 6/2005 | Kenda et al. | .................. | 514/394 |

FOREIGN PATENT DOCUMENTS

EP      252885          * 7/1987
WO     WO 03/094913    * 11/2003

OTHER PUBLICATIONS

Pirkle et al. (Chem. Rev. 1989, 89, 347-362).*
Pirkle et al.(J. Am. Chem. Soc. 1981, 103, 3964-3966 0.*
Kenda et al. (J. Med. Chem. 2004, 47, 530-549).*

* cited by examiner

*Primary Examiner* — Kristin Vajda
*Assistant Examiner* — Valerie Rodriguez-Garcia
(74) *Attorney, Agent, or Firm* — McDonnell Boehnen Hulbert & Berghoff LLP

(57) ABSTRACT

The present invention relates to optically enriched or substantially optically pure 4-substituted-pyrrolidin-2-ones of formula (III), and their uses for the synthesis of 2-oxo-pyrrolidin-1-yl derivatives.

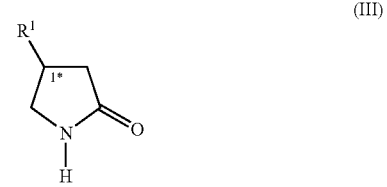

(III)

5 Claims, No Drawings

2-OXO-1-PYRROLIDINE DERIVATIVES, PROCESSES FOR PREPARING THEM AND THEIR USES

The present invention relates to 4-substituted-pyrrolidin-2-ones and their uses for the manufacture of 2-oxo-pyrrolidin-1-yl derivatives.

2-oxo-pyrrolidin-1-yl derivatives, such as (2S)-2-[(4R)-2-oxo-4-propyl-pyrrolidin-1-yl]butanamide (1) and (2S)-2-[(4S)-4-(2,2-difluorovinyl)-2-oxopyrrolidin-1-yl]butanamide (II), known respectively under the international non propriety names of brivaracetam (I) and seletracetam (II), as well as their processes and uses as pharmaceuticals are described in the international patent application having publication number WO 01/62726. These derivatives are particularly suited for treating neurological disorders.

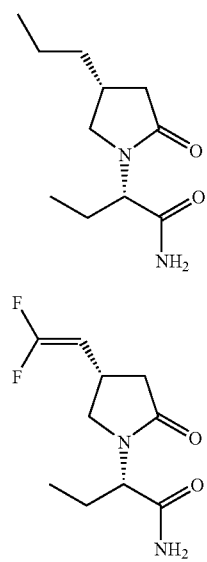

International patent applications published respectively under number WO 01/64637 and WO 03/014080 describe processes of manufacturing of 2-oxo-pyrrolidin-1-yl derivatives using pyrrolidine-2-ones.

We have now surprisingly found that optically enriched 4-substituted-pyrrolidin-2-ones or optically pure 4-substituted-pyrrolidin-2-ones may be used as starting materials for the synthesis of 2-oxo-pyrrolidin-1-yl derivatives.

In one aspect the present invention relates to optically enriched 4-substituted-pyrrolidin-2-ones of formula (III),

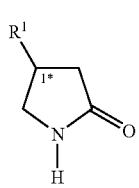

wherein $R^1$ is ethyl, n-propyl, a $C_{1-3}$ alkyl substituted by at least one halogen or a $C_{2-4}$ alkenyl.

The term "alkyl", as used herein, is a group which represents saturated, monovalent hydrocarbon radicals having straight (unbranched), branched or cyclic moieties, or combinations thereof. Preferred alkyl comprises 1-3 carbons. Optionally, alkyl groups may be substituted by 1 to 5 substituents independently selected from the group consisting of halogen, hydroxy, alkoxy, ester, acyl, cyano, acyloxy, acid, amide or amino group. Preferred alkyl groups are methyl, ethyl, n-propyl, optionally substituted by at least one halogen atom.

The term "alkenyl" as used herein represents unsubstituted or substituted branched, unbranched or cyclic hydrocarbon radicals or combinations thereof having at least one double bond. Preferred alkenyl comprises 2 to 4 carbons. "Alkenyl" moieties may be optionally substituted by 1 to 5 substituents independently selected from the group consisting of halogen, hydroxy, alkoxy, ester, acyl, cyano, acyloxy, carboxylic acid, amide or amino group.

Preferred alkenyl is substituted by at least one halogen. More preferred alkenyl is substituted by at least two halogens. Most preferred alkenyl is 2,2-difluorovinyl.

The term "halogen", as used herein, represents an atom of fluorine, chlorine, bromine, or iodine. Preferred halogen is fluorine or bromine.

The term "hydroxy", as used herein, represents a group of formula —OH.

The term "alkoxy", as used herein, represents a group of formula —OR$^a$ wherein R$^a$ is $C_{1-4}$ alkyl as defined above The term "acyl" as used herein, represents a group of formula R$^b$ CO—, wherein R$^b$ represents a $C_{1-4}$ alkyl as defined above.

The term "ester", as used herein, represents a group of formula —COOR$^c$ wherein R$^c$ represents a $C_{1-4}$ alkyl as defined above.

The term "cyano" as used herein represents a group of formula —CN.

The term "acyloxy" as used herein represents a group of formula —O—COR$^d$, wherein R$^d$ is a $C_{1-4}$ alkyl as defined above or an aryl group.

The term "aryl" as used herein, represents an organic radical derived from an aromatic hydrocarbon by removal of one hydrogen, for example a phenyl.

The term "carboxylic acid" as used herein represents a group a group of formula —COOH.

The term "amino group", as used herein, represents a group of formula —NIH$_2$, NHR$^e$ or NR$^f$R$^e$ wherein R$^e$ and R$^f$ are alkyl groups as defined above in the specification.

The term "amide", as used herein, refers to a group of formula —NH$_2$—CO—, —NHR$^g$, or —NR$^g$R$^h$—CO, wherein R$^g$ and R$^h$ are alkyl groups as defined above in the specification.

Compounds of formula (III) have at least one stereogenic center in their structure which is indicated by (1*). The stereogenic center may be present in R or S configuration, said R and S notation being used in accordance with the rules described in Pure. Appl. Chem., 45 (1976) 11-30.

The expression "optically enriched" as used herein when referring to a particular compound means that more than 50%, preferably more than 75%, more preferably more than 85%, most preferably more than 94% of the compound has the stereogenic center indicated by (1*) in a given configuration (R) or (S).

In a preferred embodiment, the present invention relates to substantially optically pure 4-substituted-pyrrolidin-2-ones of formula (III),

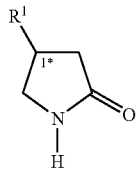

(III)

wherein $R^1$ is ethyl, n-propyl, a $C_{1-3}$ alkyl substituted by at least one halogen or a $C_{2-4}$ alkenyl.

The expression "substantially optically pure" as used herein when referring to a particular compound means that at least 95%, preferably at least 96%, more preferably at least 97%, most preferably at least 98%, even most preferably at least 99% of the compound has the stereogenic center indicated by (1*) in a given configuration (R) or (S).

Optically enriched or substantially optically pure 4-substituted-pyrrolidin-2-ones are particularly useful for the synthesis of 2-oxo-pyrrolidin-1-yl derivatives that may be used for the treatment, or used for the manufacture of a medicament for the treatment of various diseases.

Preferably, $R^1$ is n-propyl or a $C_{2-4}$ alkenyl.

More preferably, $R^1$ is n-propyl or a $C_{2-4}$ alkenyl, said $C_{2-4}$ alkenyl being substituted by at least one halogen.

Most preferably, $R^1$ is n-propyl or a $C_2$ alkenyl, said $C_2$ alkenyl being substituted by at least one halogen.

In a particular embodiment, $R^1$ is n-propyl or a $C_2$ alkenyl, said $C_2$ alkenyl being substituted by at least two halogens.

Best $R^1$ is n-propyl or 2,2-difluorovinyl.

Preferably, when $R^1$ is n-propyl, at least 95%, preferably at least 96%, more preferably at least 97%, most preferably at least 98%, even most preferably at least 99% of the compound of formula (III) has the stereogenic center indicated by (1*) in configuration (R).

Preferably, when $R^1$ is 2,2-difluorovinyl, at least 95%, preferably at least 96%, more preferably at least 97%, most preferably at least 98%, even most preferably at least 99% of the compound of formula (III) has the stereogenic center indicated by (1*) in configuration (S).

In a particular embodiment, the present invention relates to compound (R)-4-propyl-pyrrolidin-2-one of formula (IIIa):

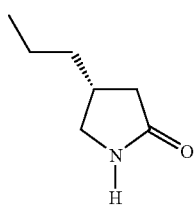

(IIIa)

Preferably, compound (IIIa) is substantially optically pure.

In another particular embodiment, the present invention relates to compound (S)-4-(2,2-difluoro-vinyl)-pyrrolidin-2-one of formula (IIIb).

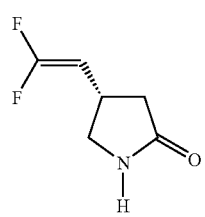

(IIIb)

Preferably, compound (IIIa) is substantially optically pure.

Substantially optically pure 4-substituted-pyrrolidin-2-ones (IIIa) and (IIIb) are particularly useful for the synthesis respectively of brivaracetam (I) and seletracetam (II).

Substantially optically pure 4-substituted-pyrrolidin-2-ones of formula (III) may be obtained by chiral separation of corresponding racemic 4-substituted-pyrrolidin-2-ones. Preferably, such chiral separation is achieved on a stationary phase selected from the group consisting of CHIRALPAK® AD, CHIRALPAK® AD-H, CHIRALCEL® OD, CHIRALCEL® OD-H, CHIRALCEL® OJ, CHIRALCEL® OJ-H, CHIRALCEL® OG, CHIRALCEL® OG-H, CHIRALCEL® OB-H which are commercially available from Daicel Chemical Industries, Ltd. (Japan).

Separation of racemic 4-substituted-pyrrolidin-2-ones may be achieved with a variety of eluting solvents. Examples of eluting solvents are alkanes, alcohols and mixtures thereof. Usually, according to the present invention, mixtures of these solvents are used in a ratio which depends upon the type of column which is used and upon the 4-substituted-pyrrolidin-2-one to be separated.

Preferably, mixtures of alkanes/alcohols in a ratio 90/10, 85/15 or 50/50 are used depending on the 4-substituted-pyrrolidin-2-one to be separated. More preferably, the alkane is selected from n-hexane, 2-methyl-pentane, n-heptane, or mixtures thereof and the alcohol is selected from methanol, ethanol, isopropanol, n-propanol or mixtures thereof. Preferred mixtures of alcohols are n-propanol/ethanol in a ratio of 75/25 or 50/50 and n-propanol/methanol in a ratio of 75/25 or 50/50.

Generally, the choice of solvent and of stationary phase will be apparent to the person skilled in the art depending on the substrate to be separated.

Alternatively, the separation step may occur on protected 2-oxo-pyrrolidin-1-yl derivatives, for example on 2-oxo-pyrrolidin-1-yl derivatives of general formula (IIIc), to afford protected substantially optically pure 2-oxo-pyrrolidin-1-yl derivatives of general formulae (IIId) and (IIIe) which are subsequently deprotected to afford the desired substantially optically pure 4-substituted-pyrrolidin-2-ones of formula (III).

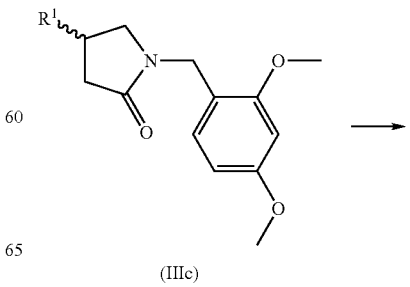

(IIIc)

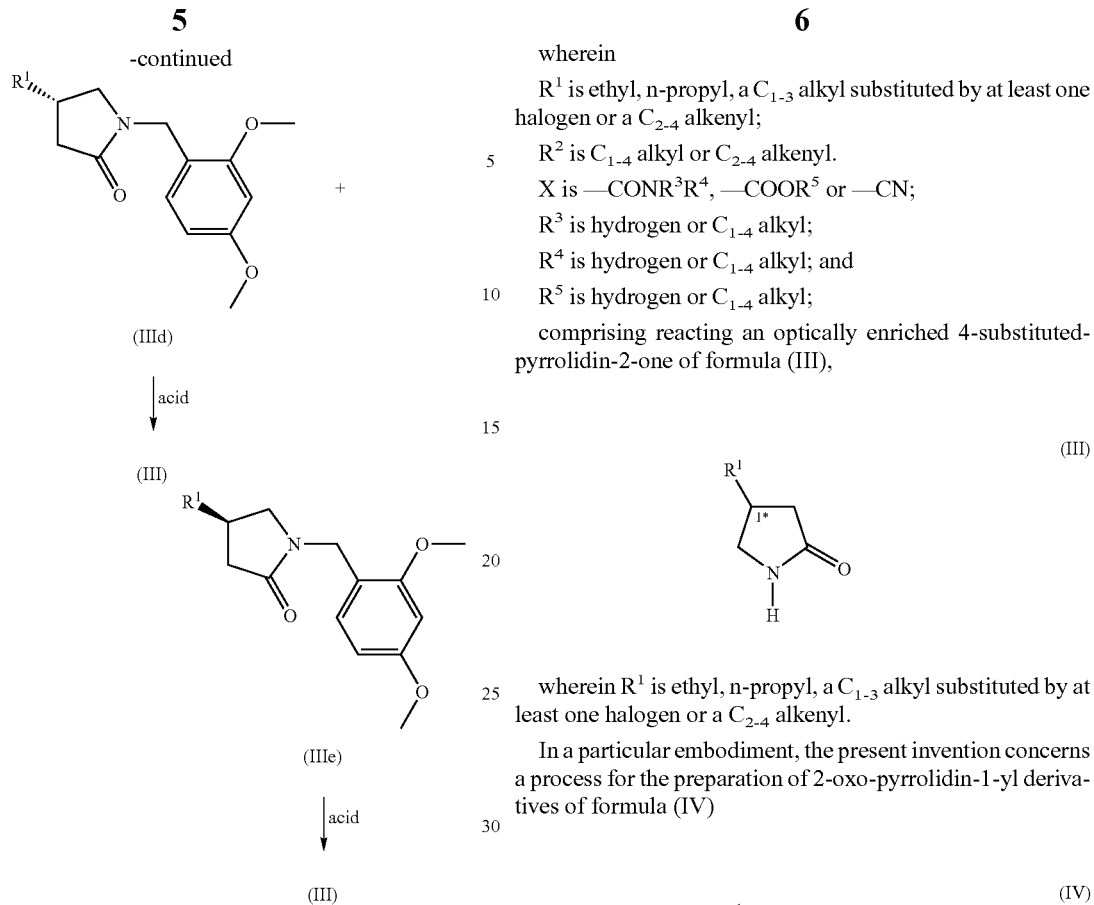

Separation of (IIIc) is generally achieved using a mixture alkane/alcohol in a ratio 50/50, preferably a mixture of hexane or heptane with ethanol, isopropanol or n-propanol in a ratio 50/50, most preferably with a mixture of heptane/isopropanol in a ratio 50/50.

Deprotection may occur by reacting 2-oxo-pyrrolidin-1-yl derivatives of general formulae (IIId) and (IIIe) with an acid, preferably trifluoroacetic acid, according to conventional methods known to the person skilled in the art.

A great variety of protecting groups may be used, the choice of which will be apparent to the skilled person in the art.

Racemic 4-substituted-pyrrolidin-2-ones may be prepared according to conventional methods known to the man skilled in the art, for example as described in Gouliaev A. H., Monster J. B., Vedso M., Senning A., Org. Prep. Proceed. Int. (1995), 27, 273-303 or in international patent application published under number WO 2005/054188.

In one aspect, the present invention concerns a process for the preparation of 2-oxo-pyrrolidin-1-yl derivatives of formula (IV)

(IV)

wherein $R^1$ is ethyl, n-propyl, a $C_{1-3}$ alkyl substituted by at least one halogen or a $C_{2-4}$ alkenyl;

$R^2$ is $C_{1-4}$ alkyl or $C_{2-4}$ alkenyl.

X is —$CONR^3R^4$, —$COOR^5$ or —CN;

$R^3$ is hydrogen or $C_{1-4}$ alkyl;

$R^4$ is hydrogen or $C_{1-4}$ alkyl; and $R^5$ is hydrogen or $C_{1-4}$ alkyl;

comprising reacting an optically enriched 4-substituted-pyrrolidin-2-one of formula (III), (III)

wherein $R^1$ is ethyl, n-propyl, a $C_{1-3}$ alkyl substituted by at least one halogen or a $C_{2-4}$ alkenyl.

In a particular embodiment, the present invention concerns a process for the preparation of 2-oxo-pyrrolidin-1-yl derivatives of formula (IV)

(IV)

wherein $R^1$ is ethyl, n-propyl, a $C_{1-3}$ alkyl substituted by at least one halogen or a $C_{2-4}$ alkenyl;

$R^2$ is $C_{1-4}$ alkyl or $C_{2-4}$ alkenyl.

X is —$CONR^3R^4$, —$COOR^5$ or —CN;

$R^3$ is hydrogen or $C_{1-4}$ alkyl;

$R^4$ is hydrogen or $C_{1-4}$ alkyl;

$R^5$ is hydrogen or $C_{1-4}$ alkyl;

comprising a reaction between an optically enriched 4-substituted-pyrrolidin-2-one of formula (III),

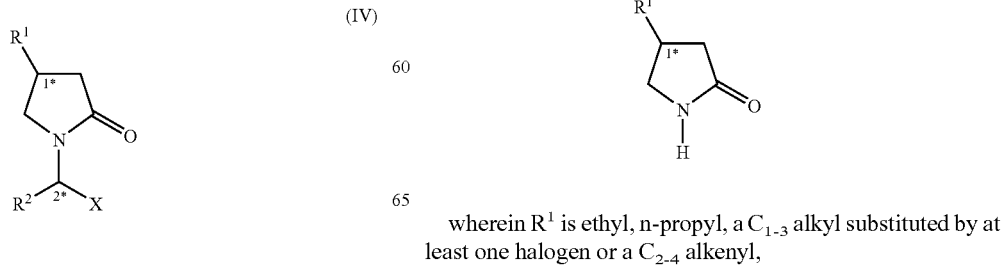

wherein $R^1$ is ethyl, n-propyl, a $C_{1-3}$ alkyl substituted by at least one halogen or a $C_{2-4}$ alkenyl, with a compound of formula (V)

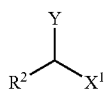
(V)

wherein
$R^2$ is $C_{1-4}$ alkyl or $C_{2-4}$ alkenyl.
$X^1$ is —$CONR^3R^4$, —$COOR^5$ or —CN;
$R^3$ is hydrogen or $C_{1-4}$ alkyl;
$R^4$ is hydrogen or $C_{1-4}$ alkyl;
$R^5$ is hydrogen or $C_{1-4}$ alkyl; and
Y is a leaving group selected from halogen, sulfonate group or —$N_2^+$.

Preferably, the process for the preparation of 2-oxo-pyrrolidin-1-yl derivatives of formula (IV) according to the present invention comprises reacting a substantially optically pure 4-substituted-pyrrolidin-2-ones of formula (III).

The term "leaving group", as used herein, has the same meaning by the person skilled in the art (Advanced Organic Chemistry: reactions, mechanisms and structure—Third Edition by Jerry March, John Wiley and Sons Ed.; 1985 page 179) and represents a group which is part of and attached to a substrate molecule; in a reaction where the substrate molecule undergoes a displacement reaction (with for example a nucleophile), the leaving group is then displaced.

The term "sulfonate group" as used herein represents a group of formula —O—$SO_2$—$R^i$ wherein $R^i$ is an alkyl or an aryl as defined hereabove in the specification. Preferred sulfonate groups are methanesulfonate, para-toluenesulfonate group or trifluoromethanesulfonate.

Compound of formula (V) wherein Y is —$N_2^+$ may be generated in situ from the corresponding amino group, by reaction with $NaNO_2$ in the presence of an acid according to methods described, for example, in the following references: J. Chem. Soc. Chem. Commun. 1976, 234; J. Am. Chem. Soc. 1949, 71, 1096; J. Am. Chem. Soc. 1990, 112(17), 6388; Helv. Chem. Acta, 1963, 46, 927 or according to any conventional methods known to the person skilled in the art Reaction of compound (III) with compound (V) occurs in the presence of a base in a solvent. Preferred base is selected from the group consisting of potassium hydride, sodium hydride, sodium methoxide, potassium methoxide, sodium isopropoxide, sodium tert-butoxide and potassium tert-butoxide.

Preferred solvent is selected from the group consisting of isopropanol, tert-butanol, dimethoxyethane and toluene.

The reaction generally occurs at a temperature comprised between 0 and 25° C.

Reaction of optically enriched or substantially optically pure 4-substituted-pyrrolidin-2-ones of formula (III) with compound of formula (V) usually affords compounds of formula (VI)

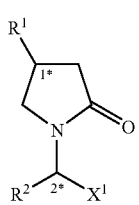
(VI)

wherein
$R^1$ is ethyl, n-propyl, a $C_{1-3}$ alkyl substituted by at least one halogen or a $C_{2-4}$ alkenyl;
$R^2$ is $C_{1-4}$ alkyl or $C_{2-4}$ alkenyl.
$X^1$ is —$CONR^3R^4$, —$COOR^5$ or —CN;
$R^3$ is hydrogen or $C_{1-4}$ alkyl;
$R^4$ is hydrogen or $C_{1-4}$ alkyl; and
$R^5$ is hydrogen or $C_{1-4}$ alkyl.

In compounds (III), (IV), (V) and (VI) according to the present invention, preferably $R^1$ is n-propyl or a $C_{2-4}$ alkenyl. More preferably, $R^1$ is n-propyl or a $C_{2-4}$ alkenyl, said $C_{2-4}$ alkenyl being substituted by at least one halogen. Most preferably, $R^1$ is n-propyl or a $C_2$ alkenyl, said $C_2$ alkenyl being substituted by at least one halogen. Particularly, $R^1$ is n-propyl or a $C_2$ alkenyl, said $C_2$ alkenyl being substituted by at least two halogens. Best $R^1$ is n-propyl or difluorovinyl.

Preferably, $R^2$ is a $C_{1-4}$ alkyl. More preferably, $R^2$ is ethyl.
Preferably, X is —$CONR^3R^4$
Preferably, $R^3$ is hydrogen.
Preferably, $R^4$ is hydrogen.
Preferably, $X^1$ is $COOR^5$.
Preferably, $R^5$ is $C_{1-4}$ alkyl. More preferably $R^5$ is methyl.
Preferably, according to the present invention, Y is halogen or a sulfonate group. More preferably, according to the present invention, Y is halogen. Most preferably, according to the present invention, Y is bromine.

Using optically enriched or substantially optically pure 4-substituted-pyrrolidin-2-ones presents the advantages of reducing the proportion of undesired stereoisomers of 2-oxo-pyrrolidin-1-yl derivatives (IV) and (VI) generated in the course of reaction, thereby increasing productivity of the overall process.

Advantageously, the process of preparation of 2-oxo-pyrrolidin-1-yl derivatives of formula (IV) according to the present invention

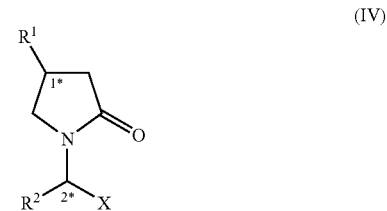
(IV)

wherein
X is —$CONR^3R^4$, and $R^3$ and $R^4$ are hydrogen
further comprises ammonolysis of compounds of formula (VI),

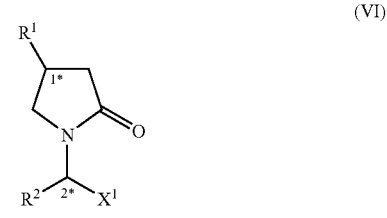
(VI)

wherein
$X^1$ is —$COOR^5$ and $R^5$ is $C_{1-4}$ alkyl.
Preferably, $R^5$ is methyl.
The ammonolysis may be performed according to conditions described in international patent application n° WO 03/014080 or according to any other conventional method known to the person skilled in the art.

Compounds of formula (IV) and compounds of formula (VI) have at least two stereogenic centers in their structure which are indicated by (1*) and (2*). The stereogenic centers may be present in R or S configuration, said R and S notation being used in accordance with the rules described in Pure. Appl. Chem., 45 (1976) 11-30.

Compounds of formula (IV) and compounds of formula (VI) may be independently a mixture of diastereoisomers.

Preferably, compounds of formula (IV) and compounds of formula (VI) are independently a mixture of epimers.

The term "epimers" as used herein, when referring to diastereoisomers, is defined as two diastereoisomers having only one stereogenic center in a different configuration one from another.

Most preferably compounds of formula (IV) and compounds of formula (VI) are independently a mixture of epimers with respect to stereogenic center (2*).

Said mixture may comprise the epimers in a ratio equal to 1. Advantageously, said mixture comprises epimers in a ratio different from 1.

Preferred epimer of compounds of formula (IV) and preferred epimer of compounds of formula (VI) is epimer having stereogenic center (2*) in (S) configuration.

In a particular embodiment, compounds of formula (IV) and compounds of formula (VI) according to the present invention are diastereoisomerically enriched.

The expression "diastereoisomerically enriched" as used herein when referring to a particular compound means that at least 95%, preferably at least 96%, more preferably at least 97%, most preferably at least 98%, even most preferably at least 99% of the compound has the stereogenic center indicated by (1*) in a given configuration (R) or (S) and that more than 50%, preferably more than 75%, more preferably more than 85%, most preferably more than 94% of the compound has the stereogenic center indicated by (2*) in a given configuration (R) or (S).

More preferably, compounds of formula (IV) and compounds of formula (VI) according to the present invention are substantially diastereoisomerically pure.

The expression "substantially diastereoisomerically pure" as used herein when referring to a particular compound means that at least 95%, preferably at least 96%, more preferably at least 97%, most preferably at least 98%, even most preferably at least 99% of the compound has the stereogenic center indicated by (1*) in a given configuration (R) or (S) and that at least 95%, preferably at least 96%, more preferably at least 97%, most preferably at least 98%, even most preferably at least 99% of the compound has the stereogenic center indicated by (2*) in a given configuration (R) or (S).

The ammonolysis may be performed on a mixture of diastereoisomers of compounds of formula (VI), on a mixture of epimers of compounds of formula (VI), on diastereoisomerically enriched compounds of formula (VI) or on diastereoisomerically pure compounds of formula (VI).

Usually, ammonolysis of diastereoisomerically enriched compounds of formula (VI) affords diastereoisomerically enriched compounds of formula (IV).

Usually, ammonolysis of substantially diastereoisomerically pure compounds of formula (VI) affords diastereoisomerically pure compounds of formula (IV).

Preferably, the ammonolysis is achieved on the mixture of epimers of compounds of formula (VI).

Generally, configuration of stereogenic center (1*) and configuration of stereogenic center (2*) of compounds of formula (IV) is the same as respectively stereogenic center (1*) and stereogenic center (2*) of compounds of formula (VI).

Substantially diastereoisomerically pure compounds of formula (IV) and diastereoisomerically pure compounds of formula (VI) may be obtained respectively by separation of the mixture of diastereoisomers of compounds of formula (IV) or of compounds of formula (VI), or alternatively by separation of respectively the mixture of epimers of compounds of formula (IV) or of compounds of formula (VI) by any conventional technique known to the man skilled in the art.

Preferably, said separation is achieved by chromatography, using either an achiral or a chiral stationary phase according to conventional methods known to the person skilled in the art.

Diastereoisomerically enriched compounds of formula (IV) and diastereoisomerically enriched compounds of formula (VI) may be converted respectively to substantially diastereoisomerically pure compounds of formula (IV) and substantially diastereoisomerically pure compounds of formula (VI) according to conventional techniques known to the person skilled in the art. This may be achieved for example by separation or recrystallisation according to conventional methods known to the person skilled in the art.

Preferably, substantially diastereoisomerically pure compounds of formula (IV) and substantially diastereoisomerically pure compounds of formula (VI) are obtained by separation respectively of diastereoisomerically enriched compounds of formula (IV) and diastereoisomerically enriched compounds of formula (VI).

Thus, in a further aspect the process according to the present invention comprises a separation step.

Configuration of stereogenic center (1*) and configuration of stereogenic center (2*) of compounds of formula (IV) and of compounds of formula (VI) may be the same or different. Preferred configuration of stereogenic center (2*) of compounds of formula (IV) and of compounds of formula (VI) is (S).

Most preferably, substantially diastereoisomerically pure compounds of formula (IV) and substantially diastereoisomerically pure compounds of formula (VI) have at least 95%, preferably at least 96%, more preferably at least 97%, most preferably at least 98%, even most preferably at least 99% of the stereogenic center indicated by (2*) in a configuration (S).

Substantially diastereoisomerically pure compounds of formula (IV) and substantially diastereoisomerically pure compounds of formula (VI) may undergo an epimerisation to afford respectively a mixture of epimers of compounds of formula (IV) or of compounds of formula (VI) as defined here above. Said mixture of epimers may be further separated to afford substantially diastereoisomerically pure compounds of formula (IV) or substantially diastereoisomerically pure compounds of formula (VI).

Generally, according to the present invention, said epimerisation affords a mixture of epimers. Usually, the ratio of epimers is less than 100, preferably less than 3, more preferably less than 2 and most preferably equal to 1.

Thus, the process according to the present invention preferably further comprises an epimerisation step.

Generally the epimerisation is achieved on the substantially diastereoisomerically pure compound of formula (IV) or on the substantially diastereoisomerically pure compound of formula (VI) which has the stereogenic center (2*) in the undesired configuration.

Therefore, preferably, the epimerisation step is achieved on substantially diastereoisomerically pure compounds of formula (IV) or on substantially diastereoisomerically pure compounds of formula (VI) wherein the stereogenic center (2*) has configuration (R).

More preferably, said epimerisation is achieved on substantially diastereoisomerically pure compounds of formula (IV) in which the stereogenic center (2*) has configuration (R).

Most preferably, said epimerisation is achieved on substantially diastereoisomerically pure compounds of formula (IV), wherein X is —CONH$_2$, and in which the stereogenic center (2*) has configuration (R).

Said epimerisation step may enable recycling of the undesired substantially diastereoisomerically pure compounds of formula (IV) or of formula (VI), thereby reducing waste on an industrial scale and thus increasing yield of production.

The epimerisation is generally achieved by reaction of a substantially diastereoisomerically pure compound of formula (IV) or a substantially diastereoisomerically pure compound of formula (VI) with a base in a solvent.

Usually, the base is selected from the group consisting of potassium hydride, sodium hydride, sodium methoxide, potassium methoxide, sodium isopropoxide, sodium tert-butoxide and potassium tert-butoxide.

When $R^1$ is a $C_{2-4}$ alkenyl, the base is preferably sodium isopropoxide, sodium tert-butoxide and potassium tert-butoxide. These bases avoid the obtention of undesirable by-products which may result from the addition of the base to the $C_{2-4}$ alkenyl.

It has surprisingly been found that such an addition may occur, for example, when sodium methoxide or potassium methoxide are reacted with a compound of formula (IV) or a compound of formula (VI) wherein $R^1$ is a $C_{2-4}$ alkenyl, particularly 2,2-difluorovinyl.

Preferred solvent is selected from the group consisting of isopropanol, tert-butanol, dimethoxyethane and toluene. More preferred solvent is isopropanol.

In a particular embodiment, the present invention concerns the use of optically enriched 4-substituted-pyrrolidin-2-ones of formula (III) as synthetic intermediates.

In a further particular embodiment, the present invention concerns the use of substantially optically pure 4-substituted-pyrrolidin-2-ones of formula (III) as synthetic intermediates.

In another aspect, the present invention concerns the use of substantially optically pure or optically enriched 4-substituted-pyrrolidin-2-ones of formula (III) for the synthesis of diastereoisomerically enriched compounds of formula (IVa) or (VIa).

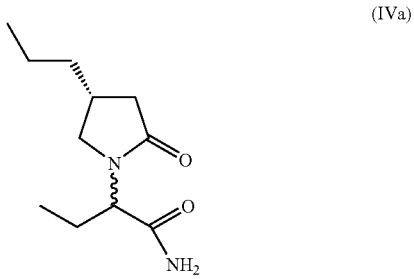

(IVa)

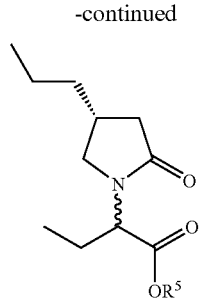

(VIa)

In another aspect, the present invention concerns the use of substantially optically pure or optically enriched 4-substituted-pyrrolidin-2-ones of formula (III) for the synthesis of diastereoisomerically enriched compounds of formula (IVb) or (VIb).

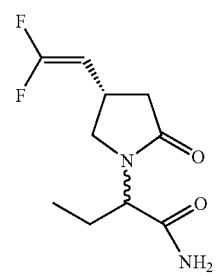

(IVb)

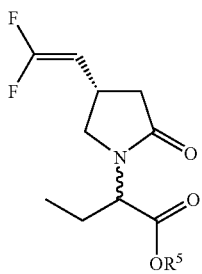

(VIb)

In compounds (VIa) and (VIb), $R^5$ is as defined here above in the specification.

Particularly, the present invention concerns the use of 4-propyl-pyrrolidin-2-one for the synthesis of brivaracetam (I).

Preferably, the present invention concerns the use of optically enriched 4-propyl-pyrrolidin-2-one for the synthesis of brivaracetam (I).

More preferably, the present invention concerns the use of substantially optically pure 4-propyl-pyrrolidin-2-one for the synthesis of brivaracetam (1).

Most preferably, the present invention concerns the use of (R)-4-propyl-pyrrolidin-2-one for the synthesis of brivaracetam (I).

In another aspect, the present invention concerns the use of 4-(2,2-difluoro-vinyl)-pyrrolidin-2-one for the synthesis of seletracetam (II).

Preferably, the present invention concerns the use of optically enriched 4-(2,2-difluoro-vinyl)-pyrrolidin-2-one for the synthesis of seletracetam (II).

More preferably, the present invention concerns the use of substantially optically pure 4-(2,2-difluoro-vinyl)-pyrrolidin-2-one for the synthesis of seletracetam (II).

Most preferably, the present invention concerns the use of (S)-4-(2,2-difluoro-vinyl)-pyrrolidin-2-one for the synthesis of seletracetam (II).

In a particular embodiment, the present invention concerns a process for the preparation of brivaracetam (I)

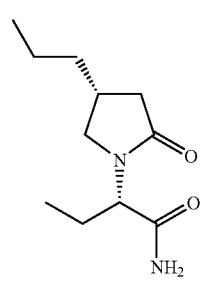

(I)

said process comprising reacting substantially optically pure (R)-4-propyl-pyrrolidin-2-one (IIIa).

In a further particular embodiment, the present invention concerns a process for the preparation of brivaracetam (I), said process comprising reaction of substantially optically pure (R)-4-propyl-pyrrolidin-2-one (IIIa) with a compound of formula (V),

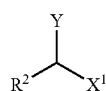

(V)

wherein

Y is a leaving group selected from halogen, sulfonate group or —$N_2^+$, $R^2$ is ethyl $X^1$ is $COOR^5$ and $R^5$ is a $C_{1-4}$ alkyl.

Preferably $R^5$ is methyl.

Preferably, according to the present invention, Y is halogen or a sulfonate group. More preferably, according to the present invention, Y is halogen. Most preferably, according to the present invention, Y is bromine.

Preferably, the process of preparation of brivaracetam (I), further comprises ammonolysis of compound of formula (VIa)

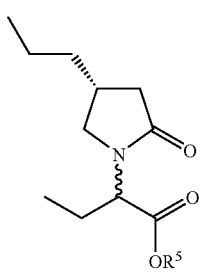

(VIa)

wherein $R^5$ is a $C_{1-4}$ alkyl to afford a mixture of brivaracetam (I) and of compound (VII)

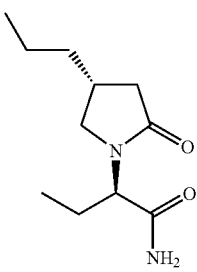

(VII)

In compound (VIa), $R^5$ is preferably a methyl.

More preferably, the process of preparation of brivaracetam (I) further comprises a separation of brivaracetam (I) and of compound (VII) as defined here above.

Most preferably, the process of preparation of brivaracetam (I) further comprises an epimerisation of compound of formula (VII) into a mixture of brivaracetam (I) and of compound of formula (VII) as defined here above, said epimerisation being followed by another separation step.

In an even more preferred embodiment, the process of preparation of brivaracetam (I) comprises iteration of said epimerisation and said another separation step.

In another particular embodiment, the present invention concerns a process for the preparation of seletracetam (II)

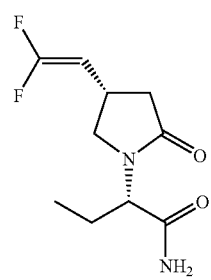

(II)

said process comprising reacting substantially optically pure (S)-4-(2,2-difluoro-vinyl)-pyrrolidin-2-one (IIIb).

In a further particular embodiment, the present invention concerns a process for the preparation of seletracetam (II), said process comprising reaction of substantially optically pure (S)-4-(2,2-(difluoro-vinyl)-pyrrolidin-2-one with a compound of formula (V),

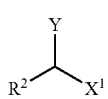

(V)

wherein

Y is a leaving group selected from halogen, sulfonate group and —$N_2^+$ $R^2$ is ethyl $X^1$ is $COOR^5$ and $R^5$ is a $C_{1-4}$ alkyl.

Preferably $R^5$ is methyl.

Preferably, according to the present invention, Y is halogen or a sulfonate group. More preferably, according to the present invention, Y is halogen. Most preferably, according to the present invention, Y is bromine Preferably, the process of preparation of seletracetam (II), further comprises amonolysis of compound of formula (VIb)

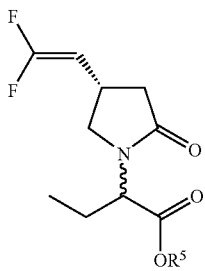
(VIb)

wherein
$R^5$ is a $C_{1-4}$ alkyl
to afford a mixture of seletracetam (II) and of compound (VIII)

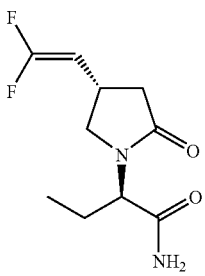
(VIII)

In compound (VIb), $R^5$ is preferably a methyl.

More preferably, the process of preparation of seletracetam (II) further comprises a separation of seletracetam (II) and of compound of formula (VIII) as defined here above.

Most preferably, the process of preparation of seletracetam (II) further comprises an epimerisation of compound of formula (VIII) into a mixture of seletracetam (I) and compound of formula (VIII) as defined here above, said epimerisation being followed by another separation step.

In an even more preferred embodiment, the process of preparation of seletracetam (II) comprises iteration of said epimerisation and said another separation step.

EXAMPLES

The following examples are provided for illustrative purposes only and are not intended, nor should they be construed, as limiting the invention in any manner. Those skilled in the art will appreciate that routine variations and modifications of the following examples can be made without exceeding the spirit or scope of the invention.

Characterization of compounds of examples 1 and 2 is achieved using the following techniques and conditions:

NMR spectra are recorded on a Bruker AC 250 Fourier Transform NMR Spectrometer fitted with an Aspect 3000 computer and a 5 mm $^1H/^{13}C$ dual probehead or Bruker DRX 400 FT NMR fitted with a SG Indigo$^2$ computer and a 5 mm inverse geometry $^1H/^{13}C/^{15}N$ triple probehead. The compound is studied in DMSO-$d_6$ (or $CDCl_3$) solution at a probe temperature of 313 K or 300 K and at a concentration of 20 mg/ml. The instrument is locked on the deuterium signal of DMSO-$d_6$ (or $CDCl_3$). Chemical shifts are given in ppm downfield from TMS taken as internal standard.

High Performance Liquid Chromatography (HPLC) analyses are performed using one of the following systems:
an Agilent 1100 series HPLC system mounted with an INERTSIL ODS 3 C18, DP 5 μm, 250×4.6 mm column. The gradient ran from 100% solvent A (acetonitrile, water, $H_3PO_4$ (5/95/0.001, v/v/v)) to 100% solvent B (acetonitrile, water, $H_3PO_4$ (95/5/0.001, v/v/v)) in 6 min with a hold at 100% B of 4 min. The flow rate is set at 2.5 ml/min. The chromatography is carried out at 35° C.
a HP 1090 series HPLC system mounted with a HPLC Waters Symmetry C18, 250×4.6 mm column. The gradient ran from 100% solvent A (MeOH, water, $H_3PO_4$ (15/85/0.001M, v/v/M)) to 100% solvent B (MeOH, water, $H_3PO_4$ (85/15/0.001 M, v/v/M)) in 10 min with a hold at 100% B of 10 min. The flow rate is set at 1 ml/min. The chromatography is carried out at 40° C.

Mass Spectrometric Measurements in LC/MS Mode are Performed as Follows:

HPLC Conditions

Analyses are performed using a WATERS Alliance HPLC system mounted with an INERTSIL ODS 3, DP 5 μm, 250×4.6 mm column.

The gradient ran from 100% solvent A (acetonitrile, water, TFA (10/90/0.1, v/v/v)) to 100% solvent B (acetonitrile, water, TFA (90/10/0.1, v/v/v)) in 7 min with a hold at 100% B of 4 min. The flow rate is set at 2.5 ml/min and a split of 1/25 is used just before API source.

MS Conditions

Samples are dissolved in acetonitrile/water, 70/30, v/v at the concentration of about 250 μgr/ml. API spectra (+ or −) are performed using a FINNIGAN (San Jose, Calif., USA) LCQ ion trap mass spectrometer. APCI source operated at 450° C. and the capillary heater at 160° C. ESI source operated at 3.5 kV and the capillary heater at 210° C.

Mass spectrometric measurements in DIP/EI mode are performed as follows: samples are vaporized by heating the probe from 50° C. to 250° C. in 5 min. EI (Electron Impact) spectra are recorded using a FINNIGAN (San Jose, Calif., USA) TSQ 700 tandem quadrupole mass spectrometer. The source temperature is set at 150° C.

Mass spectrometric measurements on a TSQ 700 tandem quadrupole mass spectrometer (Finnigan MAT, San Jose, Calif., USA) in GC/MS mode are performed with a gas chromatograph model 3400 (Varian, Walnut Creek, Calif., USA) fitted with a split/splitless injector and a DB-5MS fused-silica column (15 m×0.25 mm I.D., 1 μm) from J&W Scientific (Folsom, Calif., USA). Helium (purity 99.999%) is used as carrier gas. The injector (CTC A200S autosampler) and the transfer line operate at 290 and 250° C., respectively. Sample (1 μl) is injected in splitless mode and the oven temperature is programmed as follows: 50° C. for 5 min., increasing to 280° C. (23° C./min) and holding for 10 min. The TSQ 700 spectrometer operates in electron impact (EI) or chemical ionization (CI/CH$_4$) mode (mass range 33-800, scan time 1.00 sec). The source temperature is set at 150° C.

Specific rotation is recorded on a Perkin-Elmer 341 polarimeter. The angle of rotation is recorded at 25° C. on 1% solutions in MeOH. For some molecules, the solvent is CH$_2$Cl$_2$ or DMSO, due to solubility problems.

Melting points are determined on a Büchi 535 or 545 Tottoli-type fusionometer, and are not corrected, or by the onset temperature on a Perkin Elmer DSC 7.

Preparative chromatographic separations are performed on silicagel 60 Merck, particle size 15-40 µm, reference 1.15111.9025, using Novasep axial compression columns (80 mm i.d.), flow rates between 70 and 150 ml/min. Amount of silicagel and solvent mixtures as described in individual procedures.

Preparative Chiral Chromatographic separations are performed on a DAICEL CHIRALPAK® AD 20 µm, 100*500 mm column using an in-house build instrument with various mixtures of lower alcohols and C$_5$ to C$_8$ linear, branched or cyclic alkanes at +350 ml/min. Solvent mixtures as described in individual procedures.

Characterization of compounds of examples 3 and 4 is achieved using the following techniques and conditions:

NMR spectra are recorded on a Bruker 400 MHz spectrometer as solutions in deuterated chloroform (CDCl$_3$). Chemical shifts are expressed in parts per million (ppm, δ) downfield from tetramethylsilane and are referenced to the deuterated solvent (CDCl$_3$).

$^1$H NMR data were reported in the order of chemical shift, multiplicity (s, singlet; d, doublet; t, triplet; q, quartet; m, multiplet; app, apparent and/or multiple resonance), coupling constant (J) in hertz (Hz) and number of protons.

High Performance Liquid Chromatography (HPLC) spectra are recorded on an Alliance Waters 2695 equipped with a Sunfire C18 (3.5 um 2.1×150 mm) column. GRAD 90/10 is a gradient method in which the gradient ran from starting solvents composition (solvent A (H$_2$O, 80% v/v), solvent B (CH$_3$CN, 10% v/v) and solvent C(H$_2$O+1% H$_3$PO$_4$ v/v, 10% v/v) to the final solvent composition (solvent A (H$_2$O, 0% v/v), solvent B (CH$_3$CN, 90% v/v) and solvent C(H$_2$O+1% H$_3$PO$_4$ v/v, 10% v/v)) in 10 minutes and it is followed by a re-equilibration period of 5 minutes in the starting solvents composition. ISO80 in an isocratic method in which the composition of the eluent is: solvent A (H$_2$O+1% H$_3$PO$_4$ v/v, 80% v/v) and solvent B (CH$_3$CN+1% H$_3$PO$_4$ v/v, 20% v/v). ISO85 in an isocratic method in which the composition of the eluent is: solvent A (H$_2$O+1% H$_3$PO$_4$ v/v, 85% v/v) and solvent B (CH$_3$CN+1% H$_3$PO$_4$ v/v, 15% v/v).

Gas chromatography spectra are recorded on an Agilent 6890 series equipped with an Altech GC DB-5MS (15 m×0.25 mm) column.

Mass spectroscopy (MS): API spectra were performed using a FINNIGAN (San Jose, Calif., USA) LCQ ion trap mass spectrometer. APCI source operated at 450° C. and the capillary heater at 160° C. The ESI source operated at 3.5 kV and the capillary heater at 210° C.

Melting points are recorded on a DSC Perkin Elmer Pyris 1.

Example 1

Synthesis of substantially optically pure (R)- and (S)-4-propyl-pyrrolidin-2-ones (IIIa) and (IIIg)

1.a. Synthesis of 3-Nitromethyl-Hexanoic Acid Ethyl Ester (B)

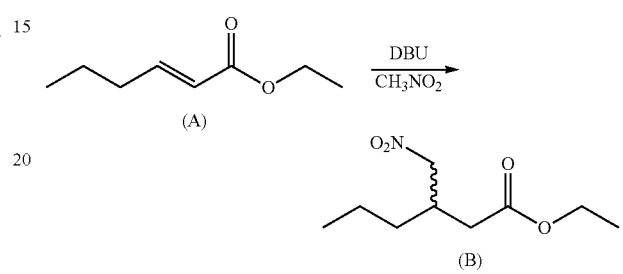

To a stirred solution of hex-2-enoic acid ethyl ester (A) (450 g, 3.164 mol, 1 eq) in nitromethane (858 ml, 15.822 mol, 5 eq) cooled at 0° C., is added dropwise, under nitrogen, 481.8 g (3.164 mol, 1 eq.) of 1.8-diazabicyclo[5.4.0]undec-7-ene (DBU). The reaction mixture is allowed to react at room temperature for 3 h and is quenched with a 6M aqueous hydrogen chloride solution to obtain pH=4. The solution is extracted with diethyl ether (500 ml+2×300 ml). The organic layers are dried with MgSO$_4$, filtered and concentrated to obtain an oil residue (672.13 g, HPLC purity=78.9%) which is purified by liquid chromatography eluting with dichloromethane. 639.41 g of 3-nitromethyl-hexanoic acid ethyl ester (B) are obtained (yield=99.4%).

GC/MS: MH$^+$=204

1.b. Synthesis of 4-propyl-pyrrolidin-2-one (C)

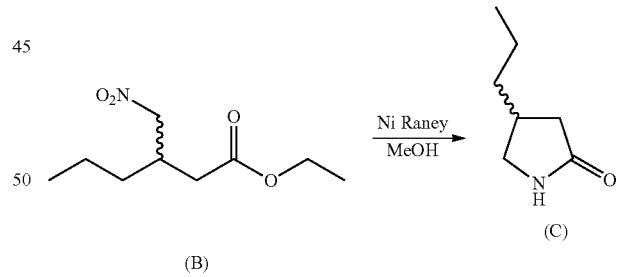

300 g (1.476 mol) of 3-nitromethyl-hexanoic acid ethyl ester (B) are diluted in methanol (500 ml). The mixture is transferred to an autoclave of 1 L. The reaction mixture is allowed to react at 55° C. under 50 bars of hydrogen pressure for 28 h. The catalyst is filtered on celite and washed with methanol. The filtrate is recovered with 500 ml of dichloromethane. Then, the solution is extracted with water (2×400 ml). The organic layers are dried with MgSO$_4$, filtered and concentrated to afford an oil residue (177.12 g, HPLC purity=82.6%) which is purified by distillation (110° C., 7.10−2 mbar). 147.82 g of (C) are obtained (Yield=78.7%).

GC/MS: M$^+$=127

¹H NMR δ0.90 (t, 11.22 Hz, 3H), 1.35 (m, 4H), 1.97 (m, 1H), 2.42 (m, 2H), 2.99 (dd, 15.13, 10.74 Hz, 1H), 3.46 (m, 1H), 6.43 (m, 1H)

1.c. Synthesis of substantially optically pure (R) and (S)-4-propyl-pyrrolidin-2-one (IIIa) and (IIIg)

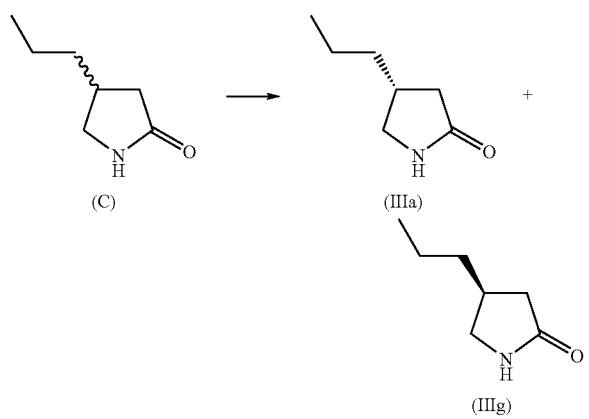

343 g of 4-propyl-pyrrolidin-2-one (C) are separated by liquid chromatography on a CHIRALPAK® AD column (100× 500 mm) eluting with propanol 8%, ethanol 2%, hexanes 90%, DEA 0.1%.
Chiral HPLC (solvent mixture: n-propanol/ethanol: 80/20)
(IIIg): retention time=6.65 minutes
(IIIa): retention time=7.81 minutes
150.4 g of (IIIg) are isolated (yield=43%)
146.0 g of (IIIa) are isolated (yield=42.5%)
[α]$_D$ of compound of formula (IIIa)=+2.33°
[α]$_D$ of compound of formula (IIIg)=−2.16°

Example 2

Synthesis of substantially optically pure (S) and (R)-4-(2,2-difluoro-vinyl)pyrrolidin-2-one (IIIb) and (IIIf)

2.a. Synthesis of toluene-4-sulfonic acid-4,4,4-trifluoro-but-2-enyl ester (E)

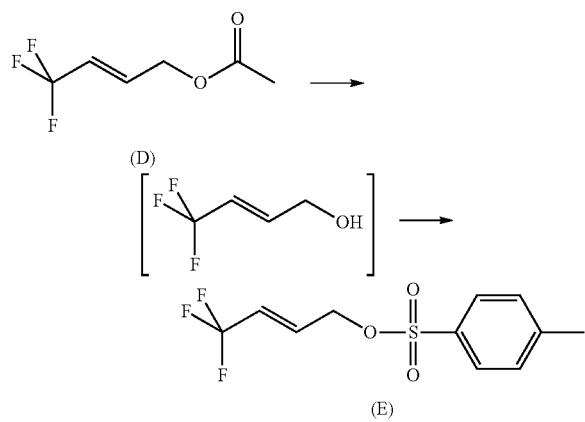

A solution of sodium hydroxide (524 g, 13.1 mol) in water (2 L) and benzyltriethylammonium bromide (88 g, 0.32 mol) are added to a stirred solution of acetic acid-4,4,4-trifluorobut-2-enyl-ester (D) (882 g, 5.25 mol) in toluene (2.8 L) at room temperature.

The reaction mixture is monitored by GC and stirred at room temperature overnight.

A solution of p-toluenesulfonyl chloride (950 g, 4.98 mol) in toluene (3 L) is slowly added dropwise at a rate such that the temperature is maintained below 25° C.

The reaction mixture is stirred for 4 hours at room temperature and is washed with water. The organic layer is dried over anhydrous MgSO$_4$ and concentrated to dryness to give 1380 g of (E) (yield=94%)
GC/MS: M⁺280

2.b. Synthesis of (2,4-dimethoxy-benzyl)-4,4,4-(trifluoro-but-2-eny)-amine (F)

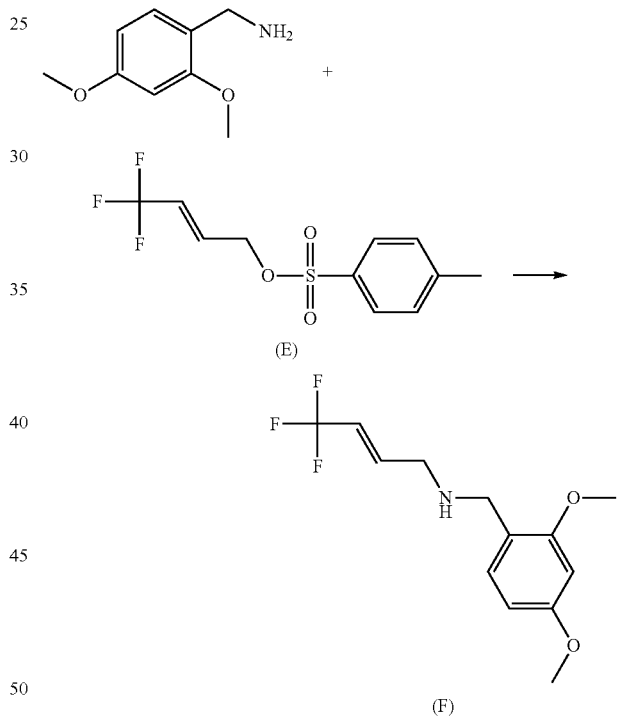

A solution of toluene-4-sulfonic acid-4,4,4-trifluoro-but-2-enyl ester (E) (642 g, 2.29 mol) in toluene (2 L) is slowly added to a stirred reaction mixture of 2,4-dimethoxy-benzylamine (401 g, 2.40 mol) and potassium carbonate (700 g, 5.06 mol) in toluene (4 L) at 65° c. The mixture is stirred at 65° C. overnight and extracted with a solution of HCl (2×5 L, 1N).

To the acid aqueous layer washed with toluene (4×7 L) is added potassium carbonate to until a pH>8 is measured in this layer. This layer is extracted with toluene (2×7 L).

The organic layer is dried over anhydrous MgSO$_4$ and concentrated to give 495 g of (F) (yield=78%)
LC/MS: MH⁺=276

2.c. Synthesis of N-(2,4-dimethoxy-benzyl)-N-(4,4,4-trifluoro-but-2-enyl)-malonamic acid methyl ester (G)

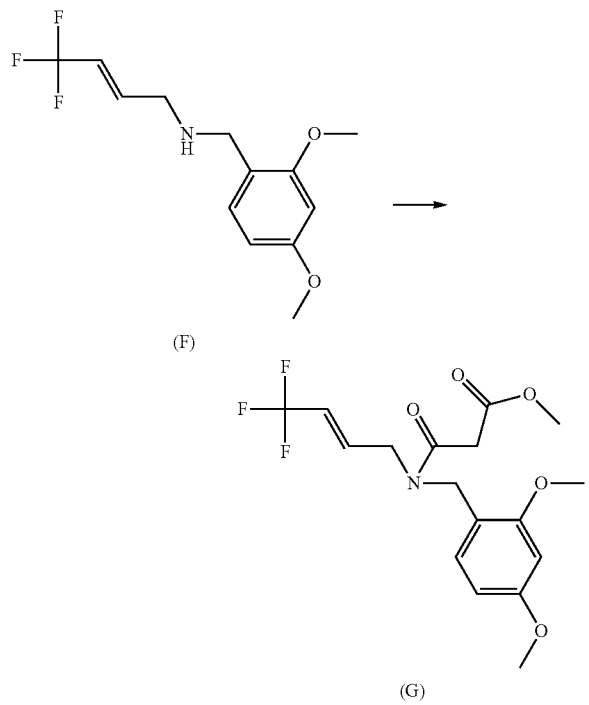

Concentrated sulfuric acid (344 g, 3.5 mol) is added dropwise to potassium monoethylmalonate (695 g, 4.08 mol) in acetonitrile (7 L) at 0° C. The solution is stirred for 30 minutes at 0° C. N,N'-carbonyldiimidazole (659 g, 4.06 mol) is added at 0° C. to the reaction mixture. The mixture is stirred for 30 minutes at 0° C. and (F) (625 g, 2.27 mol) is added. After 30 minutes at 0° C., the insoluble precipitate is removed by filtration. The filtrate is concentrated to dryness. To the residue is added toluene and this solution is washed with water and with a solution of HCl (1N). The organic layer is dried over anhydrous MgSO$_4$ and concentrated to give 888 g of (G) (yield=100%)

LC/MS: MH$^+$=376

2.d. Synthesis of 4-(2,2-difluoro-vinyl)-1-(2,4-dimethoxy-benzyl)-2-oxo-pyrrolidine-3-carboxylic acid ethyl ester (H)

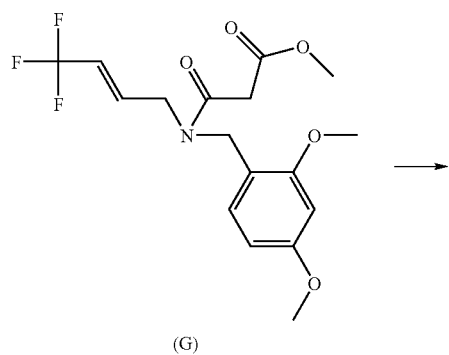

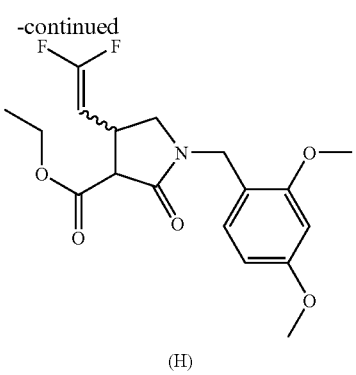

Benzyltriethylammonium bromide (92 g, 1.04 mol) and potassium carbonate (188 g, 1.36 mol) are added to a stirred refluxed solution of (G) (779 g, 2.00 mol) in acetone (4 L).

After 4 hours, 200 g of potassium carbonate is added. The reaction mixture is stirred and refluxed overnight. 200 g of potassium carbonate is added twice (every 4 hours). The insoluble precipitate is removed by filtration. The filtrate is dried over anhydrous MgSO$_4$ and concentrated to give 748 g of (H). The product is used as such in the next reaction.

LC/MS: MH$^+$=370 (two peaks)

2.e. Synthesis of 4-(2,2-difluoro-vinyl)-1-(2,4-dimethoxy-benzyl)-2-oxo-pyrrolidine-3-carboxylic acid (K)

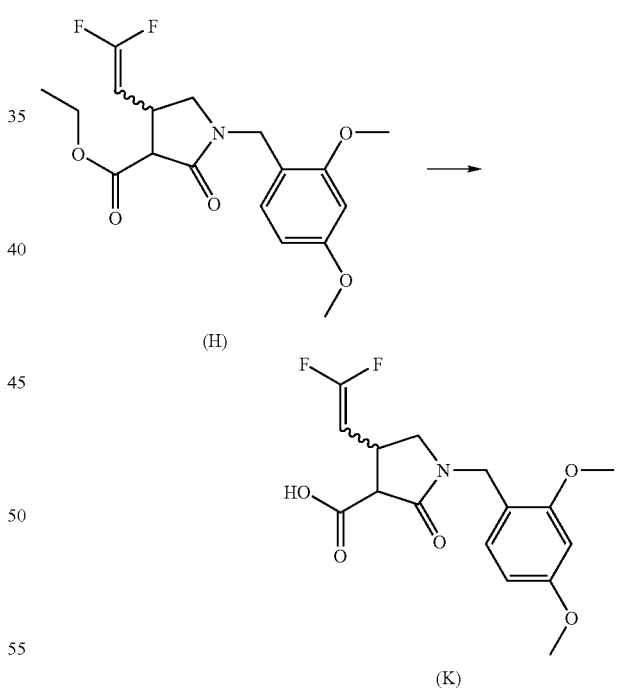

A solution of potassium carbonate (581 g, 4.20 mol) in water (4 L) is added to a stirred refluxed solution of (H) in methanol (1 L). The mixture is stirred for 18 h, washed with toluene (2×5 L) and acidified to a pH<2 with concentrated HCl (750 mL). The aqueous layer is extracted with ethyl acetate. This organic layer is washed with water, dried over anhydrous MgSO$_4$ and concentrated to give 615 g of (K) (yield=89%)

LC/MS MH$^+$=342 (two peaks)

2.f. Synthesis of 4-(2,2-difluoro-vinyl)-1-(2,4-dimethoxy-benzyl)pyrrolidin-2-one (IIIc)

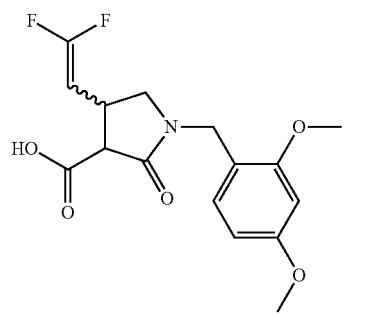

(K)

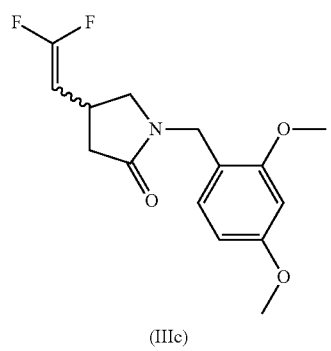

(IIIc)

A suspension of (K) in methyl isobutyl ketone (MIBK-5 L) is heated at 116° C. overnight. Evaporation of the solvent gives 564 g of (IIIc). The product is used in the next reaction without further purification.

LC/MS: MH$^+$=298

$^1$H NMR: δ2.20 (dd, 16.60, 8.05 Hz, 1H), 2.62 (dd, 16.60, 8.80 Hz, 1H), 2.98 (dd, 9.81, 7.04 Hz, 1H), 3.09 (d, 8.05 Hz, 1H), 3.44 (m, 1H), 3.79 (s, 3H), 3.81 (s, 3H) 4.18 (m, 1H), 4.41 (s, 2H), 6.45 (m, 2H), 7.14 (m, 1H)

2.g. Synthesis of (R)-4-(2,2-difluoro-vinyl)-1-(2,4-dimethoxy-benzyl)-pyrrolidin-2-one (IIId) and (S)-4-(2,2-difluoro-vinyl)-1-(2,4-dimethoxy-benzyl)-pyrrolidin-2-one (IIIe)

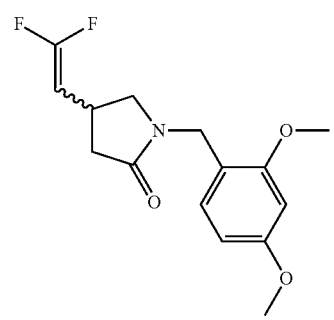

(IIIc)

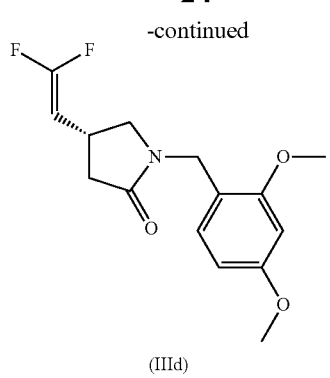

(IIId)

+

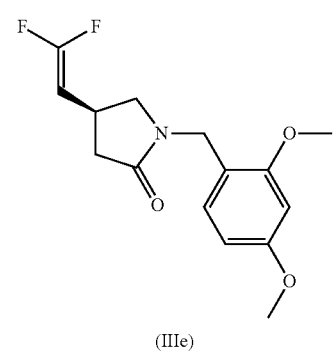

(IIIe)

(IIId) and (IIIe) are obtained by separation of (IIIc) by liquid chromatography on column CHIRALPAK® AS-H (mixture of i-PrOH 50%-heptane 50% as an eluent solvent)

Chiral HPLC: (IIId): retention time=14.65 minutes; [α]$_D$: +4.37°

(IIIe): retention time=22.56 minutes; [α]$_D$: −3.76°

2.h. Synthesis of substantially optically pure (S)-4-(difluoro-vinyl)-pyrrolidin-2-one (IIIb)

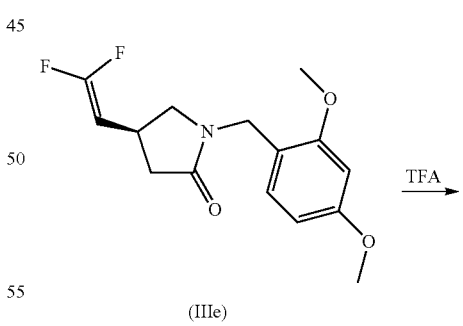

(IIIe)

TFA →

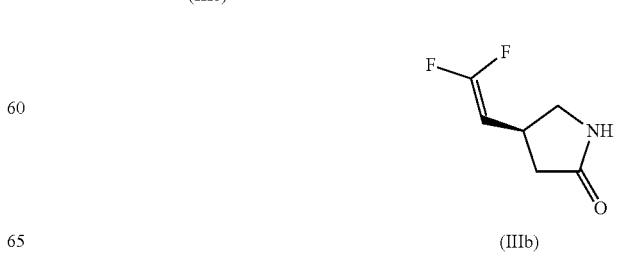

(IIIb)

21.69 g (73 mmol) of (IIIe) is refluxed in 100 ml of trifluoroacetic acid (TFA) at 80° C. for 1 hour. The reaction mixture is then cooled to room temperature under a flow of nitrogen. The solvent is removed under reduced pressure. The residue is poured into water (250 ml) and quenched with sodium hydrogenocarbonate until a pH=8 is obtained. The resulting heterogeneous mixture is filtered and the aqueous phase extracted with dichloromethane (4×250 ml). The resulting organic phase is dried over MgSO$_4$, filtered and the volatiles removed under reduced pressure. The residue is purified using silica gel column chromatography (dichloromethane/methanol 98.5/1.5 as eluting solvent) to give 6.2 g (yield=58%) of (IIIb).

NMR$^1$H: δ2.20 (dd, 16.60, 8.05 Hz, 1H), 2.62 (dd, 16.60, 8.80 Hz, 1H), 2.98 (dd, 9.81, 7.04 Hz, 1H), 3.09 (d, 8.05 Hz, 1H), 3.44 (m, 1H), 3.79 (s, 3H), 3.81 (s, 3H) 4.18 (m, 1H), 4.41 (s, 2H), 6.45 (m, 2H), 7.14 (m, 1H)

(IIIb): retention time=8.9 minutes; [α]$_D$=−6.51°

2.i. Synthesis of substantially optically pure (R)-4-(difluoro-vinyl)-pyrrolidin-2-one (IIIf)

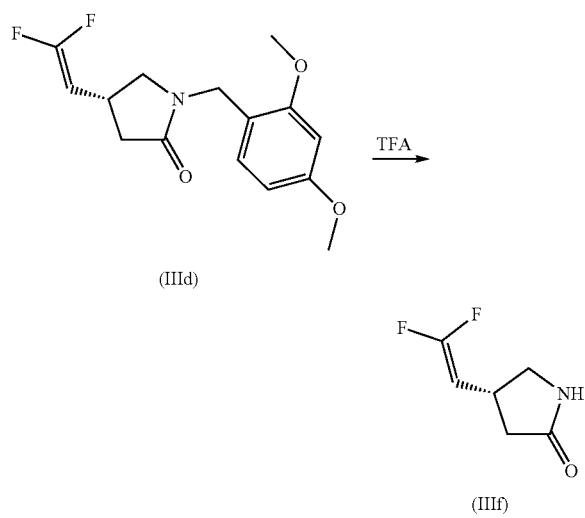

21.42 g (72 mmol) of (IIId) is refluxed in 100 ml of trifluoroacetic acid at 80° C. (TFA) for 1 hour. The reaction mixture is then cooled to room temperature under a flow of nitrogen. The solvent is removed under reduced pressure. The residue is poured into water (250 ml) and quenched with sodium hydrogenocarbonate until a pH=8 are obtained. The resulting heterogeneous mixture is filtered and the aqueous phase is extracted with dichloromethane (4×250 ml). The resulting organic phase is dried over MgSO$_4$, filtered and the volatiles removed under reduced pressure. The residue is purified using silica gel column chromatography (dichloromethane/methanol 98.5/1.5 as eluting solvent) to give 7.5 g (yield=72%) of (IIIf).

NMR$^1$H: δ2.20 (dd, 16.60, 8.05 Hz, 1H), 2.62 (dd, 16.60, 8.80 Hz, 1H), 2.98 (dd, 9.81, 7.04 Hz, 1H), 3.09 (d, 8.05 Hz, 1H), 3.44 (m, 1H), 3.79 (s, 3H), 3.81 (s, 3H) 4.18 (m, 1H), 4.41 (s, 2H), 6.45 (m, 2H), 7.14 (m, 1H)

(IIIf): retention time=10.1 minutes; [α]$_D$=+6.64°

Example 3

Synthesis of Brivaracetam (I)

3.a. Synthesis of (S) and (R) 2-((R)-2-oxo-4-propyl-pyrrolidin-1-yl)-butyric acid methyl ester (VIaa) and (VIab)

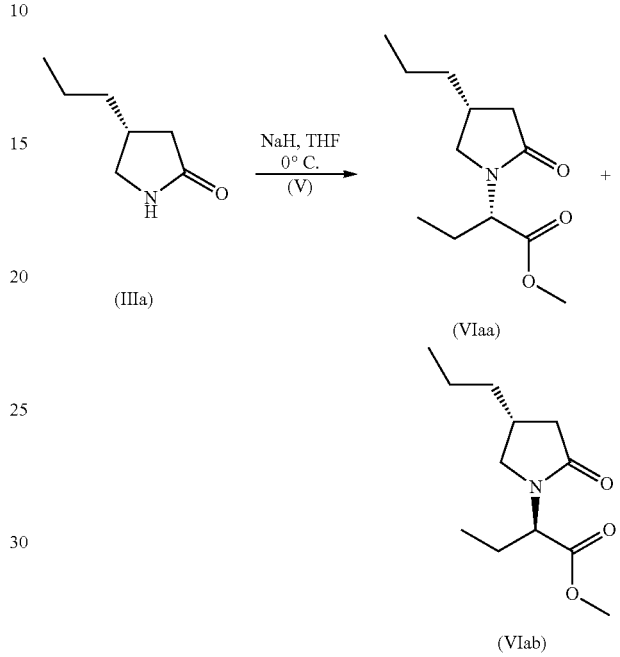

A slurry of 60% sodium hydride suspension in mineral oil (0.94 g, 23.4 mmol) in tetrahydrofuran (30 mL) is cooled at 0° C. under a nitrogen atmosphere. A solution of substantially optically pure (R)-4-propyl-pyrrolidin-2-one (IIIa) (2 g, 15.7 mmol) in tetrahydrofuran (2 mL) is added over a 15 minutes period. The reaction mixture is stirred 10 min at 0° C. then a solution of methyl-2-bromo-butyric acid methyl ester (V) (3.69 g, 20.4 mmol) in tetrahydrofuran (2 mL) was added over a 20 minutes period. The reaction mixture is stirred at 0° C. until maximum conversion of starting material and the reaction mixture is then allowed to warm to room temperature and diluted with water (20 mL). Tetrahydrofuran is removed by evaporation and the residue is extracted with isopropyl acetate (20 ml+10 mL). The combined organic layers are dried on anhydrous magnesium sulfate and evaporated to afford 3 g (13.2 mmol, 86%) of a mixture of epimers of compound (VIa), as a mixture respectively of epimer (VIaa) and epimer (VIab).

$^1$H NMR (400 MHz, CDCl$_3$) of the mixture of epimers (VIaa) and (VIab): δ=4.68 (dd, J=10.8, J=5.1, 2×1H); 3.71 (s, 2×3H); 3.60 (t app, J=8.2, 1H); 3.42 (t app, J=8.7, 1H); 313 (dd, J=9.2, J=6.8, 1H); 2.95 (dd, J=9.2, J=6.8, 1H); 2.56 (dd, J=16.6, J=8.7, 2×1H); 2.37 (dm, 2×1H); 2.10 (m, 2×1H); 2.00 (m, 2×1H); 1.68 (m, 2×1H); 1.46 (m, 2×2H); 1.36 (m, 2×2H); 0.92 (m, 2×6H).

$^{13}$C NMR (400 MHz, CDCl$_3$) of the mixture of epimers (VIaa) and (VIab): δ=175.9; 175.2; 171.9; 55.3; 52.4; 49.8; 49.5; 38.0; 37.8; 37.3; 36.9; 32.5; 32.2; 22.6; 22.4; 21.0; 14.4; 11.2; 11.1

HPLC (GRAD 90/10) of the mixture of epimers (VIaa) and (VIab): retention time=9.84 minutes (100%)

GC of the mixture of epimers (VIaa) and (VIab): retention time=13.33 minutes (98.9%)

MS of the mixture of epimers (VIaa) and (VIab) (ESI): 228 MH+

3.b. Ammonolysis of Compound of the Mixture of (VIaa) and (VIab)

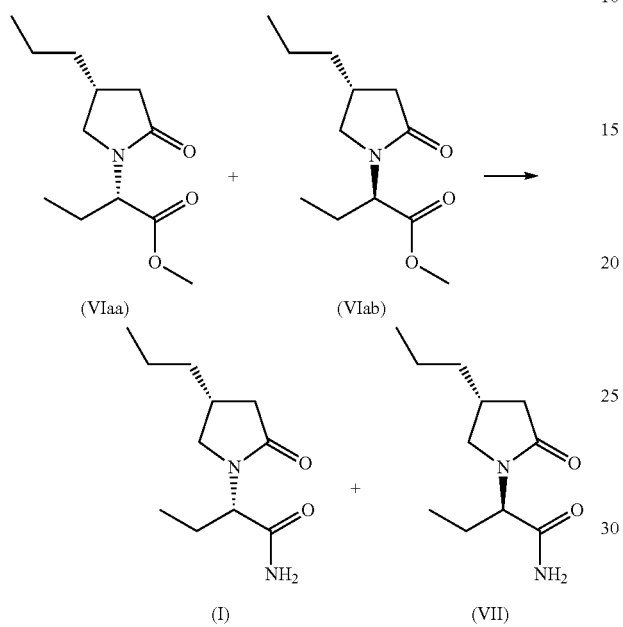

A solution of (VIaa) and (VIab) obtained in previous reaction step (1.46 g, 6.4 mmol) in aqueous ammonia 50% w/w (18 mL) at 0° C. is stirred at room temperature for 5.5 hours. A white precipitate that appears during the reaction, is filtered off, is washed with water and is dried to give 0.77 g (3.6 mmol, yield=56%) of white solid which is a mixture of brivaracetam (I) and of compound (VII) in a 1:1 ratio.

$^1$H NMR of the mixture (I) and (VII) (400 MHz, CDCl$_3$): δ=6.36 (s, broad, 1H); 5.66 (s, broad, 1H); 4.45 (m, 1H); 3.53 (ddd, J=28.8, J=9.7, J=8.1, 1H); 3.02 (m, 1H); 2.55 (m, 1H); 2.35 (m, 1H); 2.11 (m, 1H); 1.96 (m, 1H); 1.68 (m, 1H); 1.38 (dm, 4H); 0.92 (m, 6H).

$^{13}$C NMR of the mixture (I) and (VII) (400 MHz, CDCl$_3$): δ=176.0; 175.9; 172.8; 172.5; 56.4; 56.3; 50.0; 49.9; 38.3; 38.1; 37.3; 37.0; 32.3; 32.2; 21.4; 21.3; 21.0; 20.9; 14.4; 10.9; 10.8

HPLC (GRAD 90/10) of the mixture of (I) and (VII) retention time=7.67 minutes (100%)

Melting point of the mixture of (I) and (VII)=104.9° C. (heat from 40° C. to 120° C. at 10° C./min)

Compounds (I) and (VII) are separated according to conventional techniques known to the skilled person in the art. A typical preparative separation is performed on a 11.7 g scale of a 1:1 mixture of compounds (I) and (VII): DAICEL CHIRAL-PAK® AD 20 μm, 100*500 mm column at 30° C. with a 300 mL/minutes debit, 50% EtOH-50% Heptane. The separation affords 5.28 g (45%) of compound (VII), retention time=14 minutes and 5.20 g (44%) of compounds (I), retention time=23 minutes.

$^1$H NMR of compound (I) (400 MHz, CDCl$_3$): δ=6.17 (s, broad, 1H); 5.32 (s, broad, 1H); 4.43 (dd, J=8.6, J=7.1, 1H); 3.49 (dd, J=9.8, J=8.1, 1H); 3.01 (dd, J=9.8, J=7.1, 1H); 2.59 (dd, J=16.8, J=8.7, 1H); 2.34 (m, 1H); 2.08 (dd, J=16.8, J=7.9, 1H); 1.95 (m, 1H); 1.70 (m, 1H); 1.47-1.28 (m, 4H); 0.91 (dt, J=7.2, J=2.1, 6H)

HPLC (GRAD 90/10) of compound (I): retention time=7.78 minutes $^1$H NMR of compound (VII) (400 MHz, CDCl$_3$): δ=6.14 (s, broad, 1H); 5.27 (s, broad, 1H); 4.43 (t app, J=8.1, 1H); 3.53 (t app, J=9.1, 1H); 3.01 (t app, J=7.8, 11H); 2.53 (dd, J=16.5, J=8.8, 1H); 2.36 (m, 1H); 2.14 (dd, J=16.5, J=8.1, 1H); 1.97 (m, 1H); 1.68 (m, 1H); 1.43 (m, 2H); 1.34 (m, 2H); 0.92 (m, 6H)

3c. Epimerisation of compound of (2R)-2-((R)-2-oxo-4-propyl-pyrrolidin-1-yl)-butyramide (VII)

Compound (VII) (200 mg, 0.94 mmol) is added to a solution of sodium tert-butoxide (20 mg, 10% w/w) in isopropanol (2 mL) at room temperature. The reaction mixture is stirred at room temperature for 18 h. The solvent is evaporated to afford 200 mg (0.94 mmol, 100%) of a white solid. Said white solid is a mixture of brivaracetam (I) and of (VII) in a ratio 49.3/50.7.

HPLC (ISO80): retention time=7.45 min (49.3%) brivaracetam (I); retention time=8.02 minutes (50.7%) compound (VII).

Example 4

Synthesis of Seletracetam (II)

4.a. Synthesis of (S) and (R) 2-[(S)-4-(2,2-difluoro-vinyl)-2-oxo-pyrrolidin-1-yl]-butyric acid methyl ester (VIba) and (VIbb)

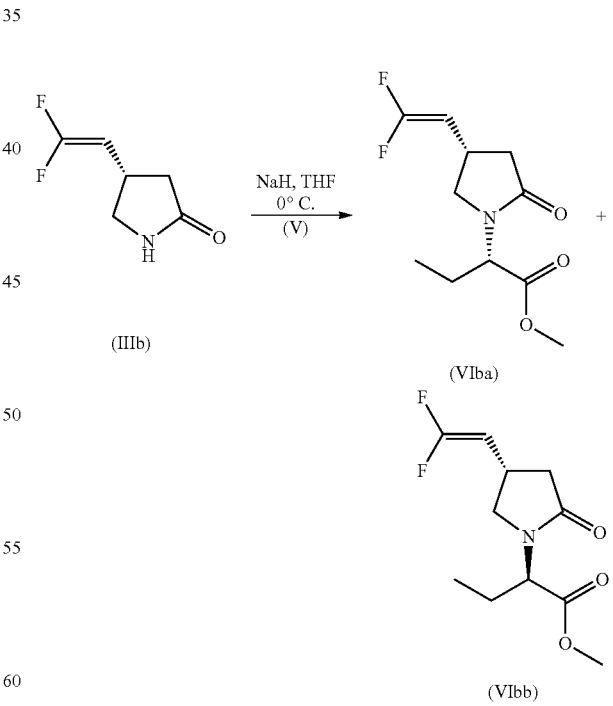

A slurry of 60% sodium hydride suspension in mineral oil (0.80 g, 20.4 mmol) in tetrahydrofuran (28 mL) is cooled at 0° C. under a nitrogen atmosphere. A solution of substantially optically pure (S)-4-(2,2-difluoro-vinyl)-pyrrolidin-2-one (IIIb) (2 g, 13.6 mmol) in tetrahydrofuran (8 mL) is added over a 30 minutes period. The reaction mixture is stirred 10 minutes at 0° C. then a solution of 2-bromo-butyric acid methyl ester (V) (3.20 g, 17.6 mmol) in tetrahydrofuran (2 mL) is added over a 15 minutes period. The reaction mixture is stirred at 0° C. for 4.5 h then the reaction mixture is allowed to warm to room temperature and diluted with water (15 mL). Tetrahydrofuran is removed by evaporation and the residue is extracted with isopropyl acetate (2×10 mL). The combined organic layers are dried over anhydrous magnesium sulfate and evaporated to afford 3 g (12.1 mmol, 89%) of compound (VIb), as a mixture respectively of epimer (VIba) and epimer (VIbb).

$^1$H NMR of the mixture of epimers (VIba) and (VIbb) (400 MHz, CDCl3): δ=4.69 (dd, J=10.8, J=5.2; 2×1H); 4.31 (m, 2×1H); 3.72 (s, 2×3H); 3.75-3.70 (m, 1H); 3.51 (t app, J=8.3, 11H); 3.30-3.05 (m, 2×2H); 2.67 (ddd, J=16.7, J=8.5, J=3.3, 2×1H); 2.26 (dd app, J=16.7, J=7.9, 2×1H); 2.02 (m, 2×1H); 1.67 (m, 2×1H); 0.93 (t, J=7.6, 2×3H).

$^{13}$C NMR of the mixture of epimers (VIba) and (VIbb) (400 MHz, CDCl$_3$): δ=174.6; 174.4; 171.8; 80.7; 80.6; 80.5; 80.4; 80.3; 80.2; 80.1; 55.4; 55.3; 52.5; 49.9; 49.4; 38.2; 38.0; 27.5; 27.4; 27.3; 27.2; 22.7; 22.5; 11.2

HPLC (GRAD 90/10) of the mixture of epimers (VIba) and (VIbb): retention time=9.07 minutes (99.1%)

GC of the mixture of epimers (VIba) and (VIbb): retention time=13.33 minutes (98.9%)

MS (APCI) of the mixture of epimers (VIba) and (VIbb): 248 MH+

4.b. Ammonolysis of the Mixture of (VIba) and (VIbb)

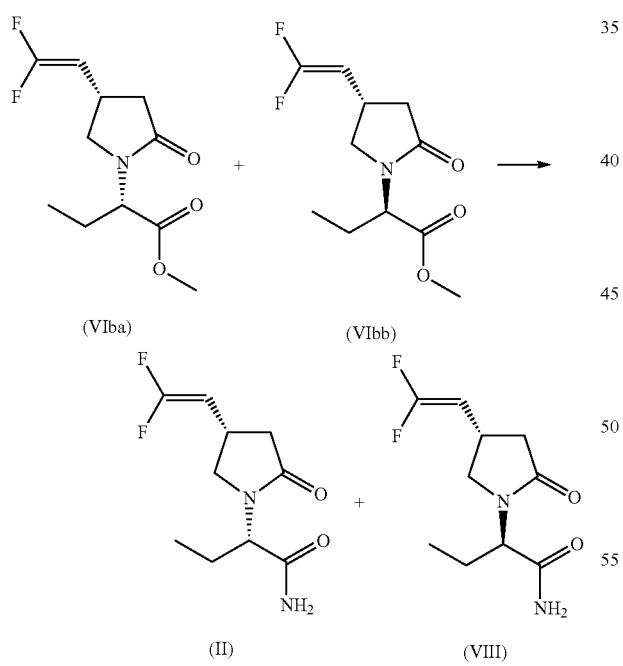

A solution of (VIba) and (VIbb) obtained in previous reaction step (1.8 g, 7.3 mmol) in aqueous ammonia 50% w/w (3 mL) at 0° C. is stirred at room temperature for 6.5 h. A white precipitate, appeared during the reaction, is filtered off, is washed with water and is dried to give 1.0 g (4.3 mmol, 59%) of white solid which is a mixture of seletracetam (II) and of compound (VIII) in a 1:1 ratio.

$^1$H NMR of the mixture of epimers (II) and (VIII) (400 MHz, CDCl$_3$): δ=6.30 (s, broad, 1H); 5.62 (s, broad, 1H); 4.47 (t, J=7.4, 1H); 4.26 (dm, J=24.1, 1H); 3.65 (dt app, J=52.4, J=8.7, 1H); 3.18 (m, 2H); 2.67 (m, 1H); 2.26 m, 1H); 1.96 (m, 1H); 1.69 (m, 1H); 0.92 (t, J=7.4, 3H).

$^{13}$C NMR of the mixture of epimers (II) and (VIII) (400 MHz, CDCl$_3$): δ=174.8; 174.6; 172.6; 172.4; 80.5; 80.3; 79.9; 56.3; 50.0; 49.8; 38.4; 38.2; 27.4; 27.2; 21.7; 21.6; 11.0; 10.9

Melting point of the mixture (II) and (VIII)=132.6° C. (heat from 35° C. to 220° C. at 10° C./min)

Compounds (II) and (VIII) are separated according to conventional techniques known to the skilled person in the art. A typical preparative separation is performed on a 7.4 g scale of a 1:1 mixture of compounds (II) and (VIII): DAICEL CHIRALPAK® AD 20 μm, 100*500 mm column at 30° C. with a 300 mL/minutes debit, 50% EtOH-50% Heptane. The separation affords 3.70 g (50%) of compound (VIII), retention time=20 minutes and 3.65 g (49%) of compounds (II), retention time=31 minutes.

$^1$H NMR of compound (II) (400 MHz, CDCl$_3$): δ=6.13 (s, broad, 1H); 5.37 (s, broad, 1H); 4.45 (t app, J=8.6, 1H); 4.24 (dd, J=24.5, J=8.8, 1H); 3.58 (m, 1H); 3.18 (m, 2H); 2.69 (dd, J=17.4, J=8.7, 1H); 2.23 (dd, J=16.5, J=8.7, 1H); 1.95 (m, 1H); 1.71 (m, 1H); 0.93 (t, J=6.8, 3H).

$^1$H NMR of compound (VIII) (400 MHz, CDCl$_3$): δ=6.09 (s, broad, 1H); 5.33 (s, broad, 1H); 4.45 (t app, J=8.6, 1H); 4.25 (dd, J=24.1, J=9.7, 1H); 3.68 (t app, J=8.6, 1H); 3.18 (m, 1H); 3.13 (m, 1H); 2.65 (dd, J=17.2, J=8.6, 1H); 2.29 (dd, J=17.2, J=8.0, 1H); 1.97 (m, 1H); 1.68 (m, 1H); 0.93 (t, J=6.9, 3H).

4c. Epimerisation of Compound of Formula (VIII)

Compound of formula (VIII) (500 mg, 2.16 mmol) is added to a solution of sodium tert-butoxide (50 mg, 10% w/w) in isopropanol (5 mL) at room temperature. The reaction mixture is stirred at room temperature for 6 h and a white precipitate appears during the reaction. The slurry is cooled to 5° C. and stirred for 30 minutes at 5° C. The precipitate is filtered off and dried to afford 150 mg (0.65 mmol, 30%) of a white solid. Said white solid is a mixture of seletracetam (II) and of compound (VIII) in a ratio 47.9/52.1.

HPLC (ISO85): retention time=7.66 min (52.1%) compound (VIII); retention time=8.23 min (47.9%) seletracetam (II).

The invention claimed is:
1. A substantially optically pure 4-substituted-pyrrolidin-2-one of formula (III),

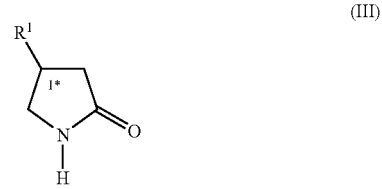

wherein R$^1$ is ethyl, n-propyl, a C$_{1-3}$ alkyl substituted by one or more halogens, or a C$_{2-4}$ alkenyl substituted by one or more halogens, and wherein 1* designates the stereogenic carbon of the pyrrolidin-2-one ring.

2. The 4-substituted-pyrrolidin-2-one of claim 1 wherein R$^1$ is n-propyl.

3. The 4-substituted-pyrrolidin-2-one of claim 1 wherein $R^1$ is 2,2-difluorovinyl.
4. A substantially optically pure compound of formula (IIIa)
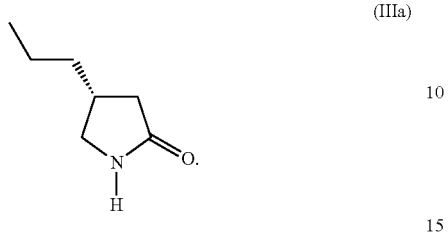
(IIIa)
5. A substantially optically pure compound of formula (IIIb)
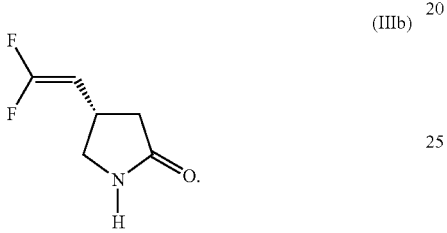
(IIIb)
* * * * *